US00PP12015P2

(12) United States Plant Patent
Reeves

(10) Patent No.: US PP12,015 P2
(45) Date of Patent: Jul. 24, 2001

(54) LIVE OAK TREE NAMED 'SDLN'

(75) Inventor: Anthony Brent Reeves, Green Cove Springs, FL (US)

(73) Assignee: Reinhold Corporation, Penney Farms, FL (US)

( * ) Notice: Subject to any disclaimer, the term of this patent is extended or adjusted under 35 U.S.C. 154(b) by 0 days.

(21) Appl. No.: 09/197,227

(22) Filed: Nov. 20, 1998

(51) Int. Cl.[7] ..... A01H 5/00
(52) U.S. Cl. ..... Plt./225
(58) Field of Search ..... Plt./225

(56) References Cited

U.S. PATENT DOCUMENTS

P.P. 11,097 * 10/1999 Sallin ..... Plt./225
P.P. 11,219 * 2/2000 Strickland ..... Plt./225

* cited by examiner

*Primary Examiner*—Bruce R. Campell
*Assistant Examiner*—Kent L. Bell
(74) *Attorney, Agent, or Firm*—Klarquist Sparkman Campbell Leigh & Whinston, LLP

(57) ABSTRACT

A distinct variety *Quercus virginiana* named 'SDLN' which is distinctive in having a dense, upright, canopy; and dominant leader; small lateral branches without included bark in the branch unions; mature dark evergreen foliage with leaves typically being about one to two inches long and about one-half inch wide; and true evergreen habit. The canopy is very dense with foliage held on shaded interior twigs.

3 Drawing Sheets

BACKGROUND OF THE INVENTION

The present invention relates to a new and distinct variety of *Quercus virginiana* (Live oak) referred to by the varietal name 'SDLN.'

The 'SDLN' initially discovered tree was found as a seedling growing in a cultivated area of the Shadowlawn Nursery in Penney Farms, Fla., among a group of cultivated Live Oak seedlings. These seedlings were grown from acorns collected from an open-pollinated unnamed, unpatented mature Live Oak tree in Leesburg, Fla. The male parent tree is unknown.

'SDLN' was observed to have an upright habit and a dominant leader, dark-green foliage color, dense foliage arrangement, and true evergreen habit. Compared to common Live Oak trees observed by the inventor, this initially discovered tree had a rapid growth rate, lacked included bark, had small diameter lateral branches, had leaves which were about one inch to two inches long by about one-half inch wide and which were consistently dark green when mature, and exhibited a dense, narrow-oval canopy. The female parent Live Oak tree is a wide-spreading (about 60 feet wide by about 40 feet tall) tree with a multiple leader branching arrangement. In comparison, the new variety has an upright habit of growth and a dominant leader. These characteristics of my new variety have been observed to be fixed and reproduces true to type in progeny asexually propagated from cuttings taken from the initially discovered tree. Asexual propagation was performed at a nursery in Penny Farms, Fla.

SUMMARY OF THE VARIETY

The 'SDLN' variety has not been observed under all growing conditions and thus variations may occur as a result of different growing conditions. The observations are of trees growing in Penney Farms, Fla.

'SDLN' has an unusually narrow, oval canopy with consistently dark green and truly evergreen foliage compared to the species in general.

The common Live Oak trees observed by me in the same geographic area of my observations of the new variety typically shed leaves in December and remain bare until new leaves appear in early February. The new 'SDLN' variety, however, sheds its leaves as it buds in February. Therefore, the tree has a true evergreen habit rather than being bare of leaves for a substantial period of time. Additionally, the leaves of 'SDLN' variety are slightly darker than those of common Live Oak trees which I have observed growing in the same general area and mature leaves have been observed to not change color significantly with the seasons.

Unlike the common Live Oak trees I have observed, the 'SDLN' variety has superior apical dominance with a single dominant leader. Common Live Oak trees observed by the inventor have a massive, spreading growth habit where the width of the canopy substantially exceeds the height of the tree. In 'SDLN,' however, the tree forms a very dense, distinctive and desirable upright, oval growth habit due to an unusual number of secondary twigs and short shoots held along main branches.

Branches arise at a wide angle (most lateral branches have branch crotch angles greater than sixty degrees), minimizing formation of included bark. Small diameter lateral branches make this plant easier to prune into a strong structure with a central leader. Unlike common Live Oak trees the inventor has observed, this new variety is easy to root. For example, in a specific observation, there was about a sixty-nine percent take for cuttings directly from the initially discovered tree and, in another observation, about eighty-two percent of the cuttings from the fourteen-month old second-generation trees rooted.

This extremely high asexual reproduction rate was obtained by preparing the cutting wood in the following manner.

a) Three inch-long stem and terminal cuttings, each with three to four leaves, were collected in the second week of May from the initially discovered tree.
b) Cuttings were quick dipped in a solution of 7500 ppm of KIBA (Potassium salt Indole-3-butyric acid) and 5000 ppm of KIAA (Potassium salt Indole-3-acetic acid).
c) Cuttings were placed in 2.25 inch Tree Band containers filled with appropriate media.
d) Plants were placed in a mist house with ten seconds mist spray every five minutes.
e) Sixty-nine percent of the cuttings rooted.
f) In the first week of July, cuttings were collected from the fourteen-month old plants originating from the initially discovered tree and were handled as described above. Eighty-two percent of these cuttings rooted.

The 'SDLN' variety has a slightly higher growth rate compared to common Live Oak trees observed by the inventor and growing in the same area. The trunk diameter, taken at 12 inches above ground of the initially discovered tree of the new variety, aged seven years and growing in Penny Farms, Fla., measured approximately six inches caliper while common Live Oak trees of the same age and observed by the inventor growing in the same area had a four to five inch caliper. The initially discovered tree has an upright habit and a dominate leader.

DETAILED BOTANICAL DESCRIPTION

Figure 1:
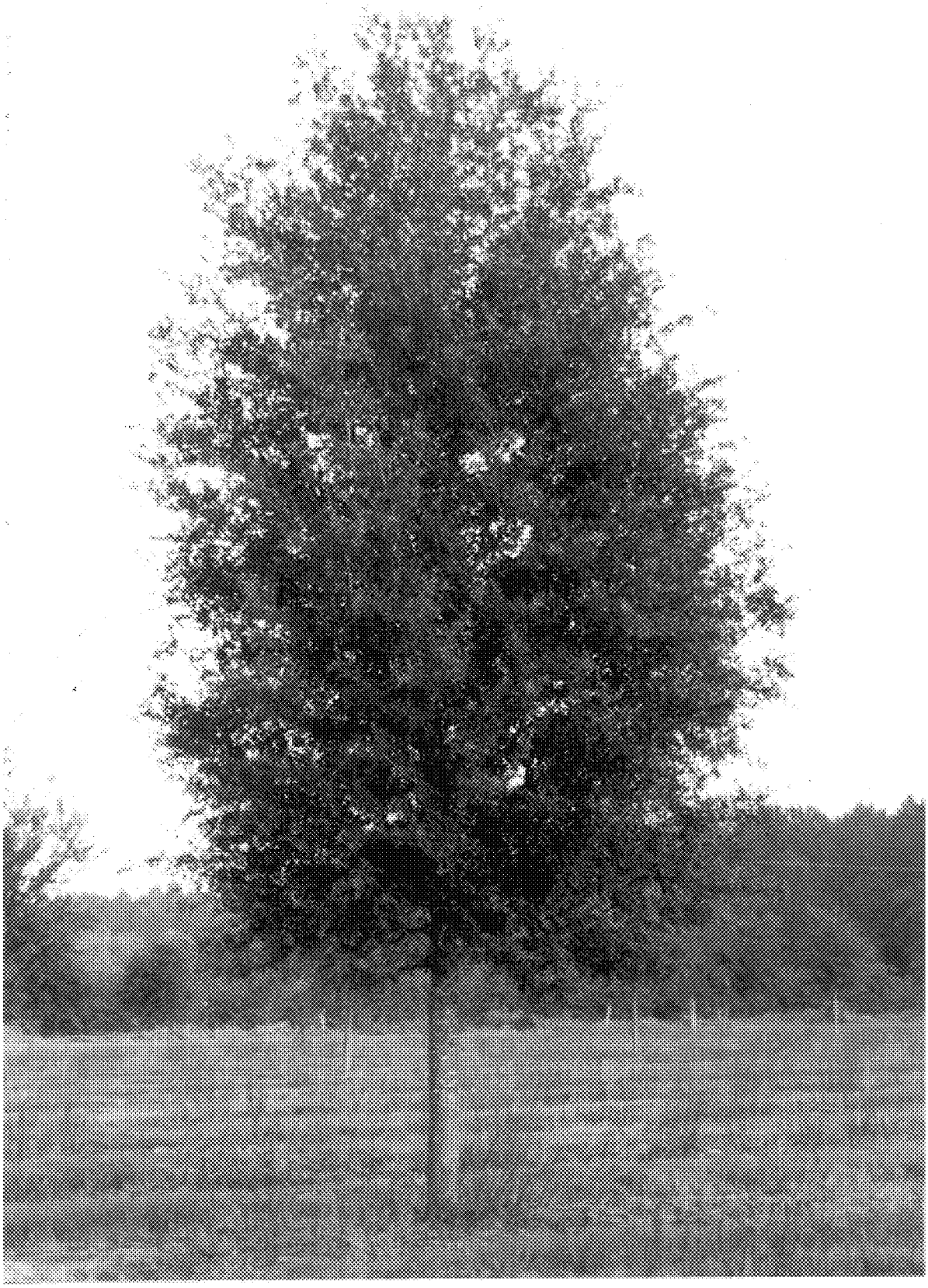
FIG. 1 depicts the initially discovered tree of my new variety showing the oval canopy shape, upright habit, and a single, dominant leader. When this picture was taken, the initially discovered tree was seven years of age, was twenty-two feet tall by ten feet wide with a six and one/thirty-second inch caliper and was growing in Penney Farms, Fla.
Figure 2:
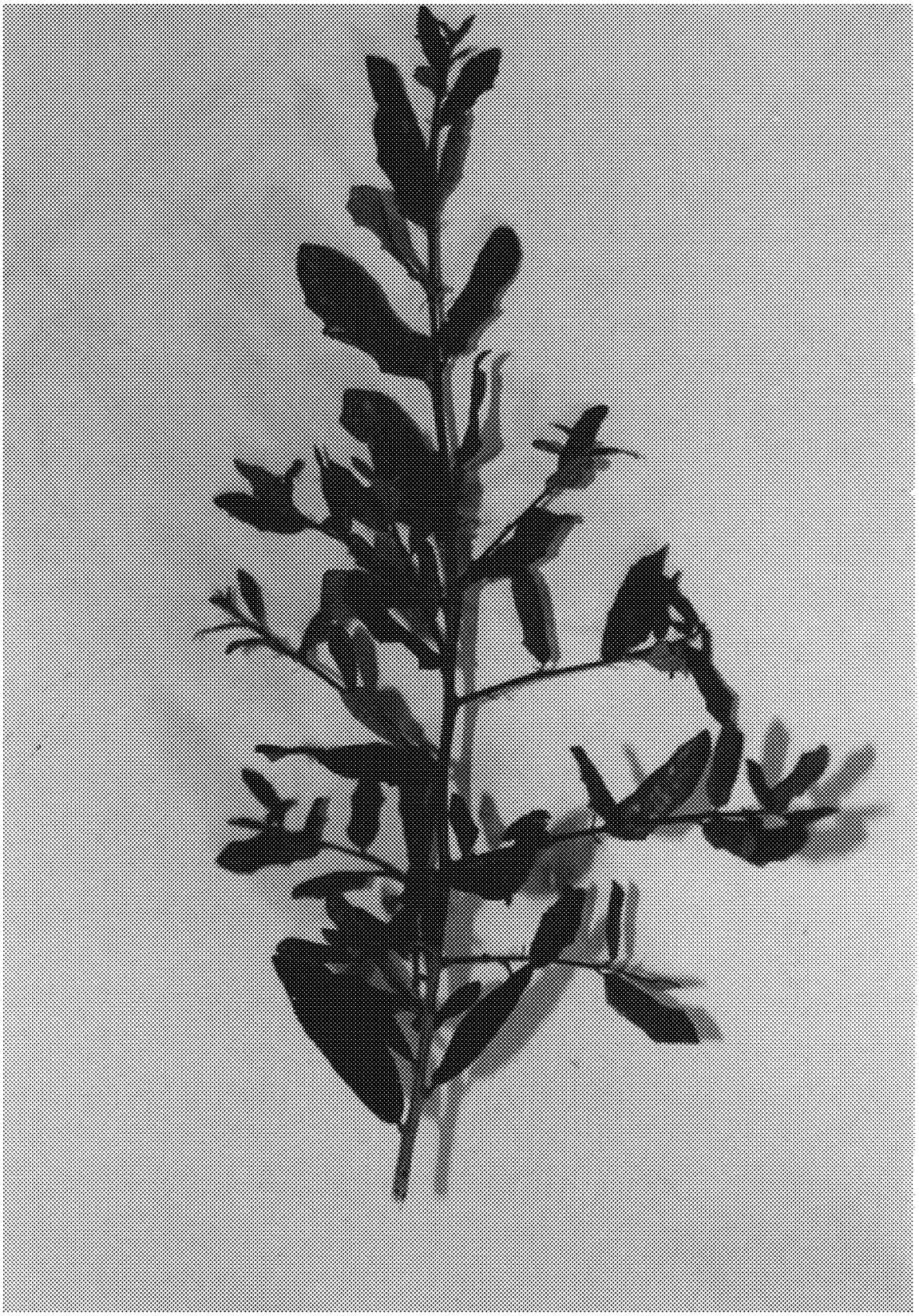
FIG. 2 shows the dense arrangement of twigs along a main branch.
Figure 3:
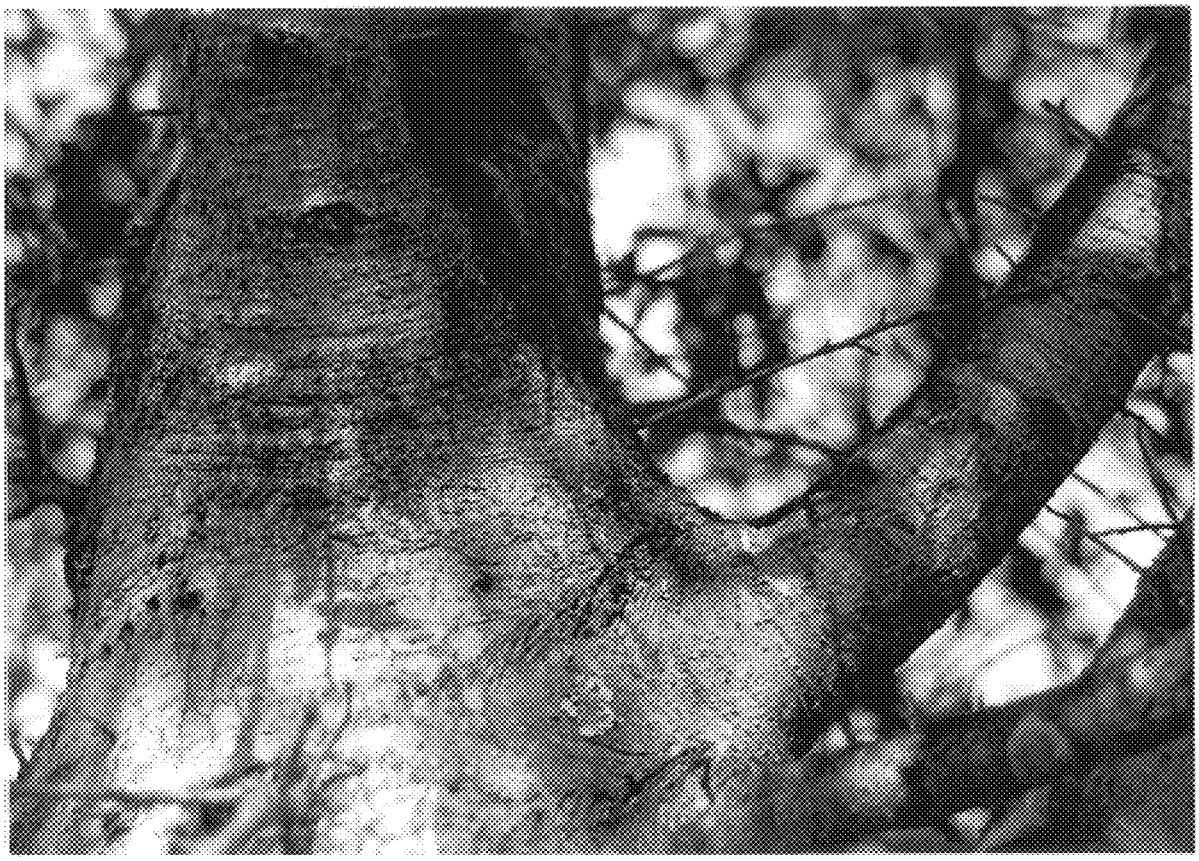
FIG. 3 shows branches arising at a wide angle and lack of included bark.

The following is a description of my new variety of Live Oak tree, at age seven years from acorn, with color terminology in accordance with The Royal Horticultural Society Colour Chart (R.H.S), except where the context indicates a term having it ordinary dictionary meaning.

All Live Oak trees of my new variety, insofar as have been observed, have been indentical in all characteristics described below. Other than as set below, as of this time no other characteristics have been observed which are different from common Live Oak trees which have been observed by the inventor.

Parentage: Seedling of unknown parentage grown from an acorn collected from an unnamed mature Live Oak tree in Leesburg, Fla.

Lacality where grown and observed: Penney Farms, Fla.

Leaves:

*Arrangement and shape.*—Alternate, simple; elliptic to oblong or obovate; base — typically acute, sometimes observed as cuneate to rounded; apex — typically obtuse, sometimes observed as acute; prominent mid-rib underneath with typically 11 to 15 main veins from the mid-rib, typically yellow-green 151C; margin — entire with occosional acute lobes or teeth; slightly tomentose underneath; stiff.

*Size.*—Length, variable, typically one to two inches; width, variable, typically one-half inch wide.

*Color.*—Evergreen tree; emerging leaves — typical upper surface maroon, like, red-purple, 178A, typical lower surface yellow-green, like 148D; young summer leaves — typical upper surface green, like 137A, typical lower surface yellow-green, like 148A; mature summer leaves — typical upper surface, green, like 136A, typical lower surface yellow — green, like 148D.

*Petiole.*—Length variable, one-sixteenth inch to one-eighth inch long is typical; width variable, one thirty-second inch to one-sixteenth inch wide is typical; upper surfave color is red-purple, like 60A; lower surface color is variable, observed from red-purple, like 60A, toyellow-green, like 151C.

Bud: Subglobose, dark brown (grayed-orange 177A), length, variable, typically one-thirty second to one-sixteenth inch; width, variable, typically one thirty-second inch to one-sixteenth inch.

Flowers and reproductive organs: Typical of species male in catkins, female in axils of leaves; initial flowering season is March in northeast Florida.

Fruit: The initially discovered tree has produced acorns typical of the species; typically one acorn per cluster, sometimes observed as two acorns per cluster; acorns mature in one growing season and typically fall from the tree in October and November in northeastern Florida; acorns are oval to ovate and short pointed at the apex; acorns are marked with a circular scar at the base, the scar is three-sixteenths to seven thirty-seconds inch across and colored greyed-orange (greyed-orange 164C); typical and observed acorns are three-quarters to seven-eights inch in length and three-eighths to seven-sixteenths inch wide; typical upper acorn coloration, under the acorn cap, colored greyed-orange (greyed-orange 165C) and typical lower acorn coloration is brown (brown 200B); typical acorn cap is three-eighths to seven-sixteenths inch in width and three-eighths inch in length; colored greyed-orange (greyed-orange 197D), and scaly with a finely serrated edge; typical acorn cap has a large number, typically 100, greyed-orange (greyed-orange 166A) spots that are one sixty-fourth to one ninety-sixth inch wide; acorn cap typically encloses one-quarter of the acorn; typical peduncle is one-quarter to three-eighths inch in length, one-sixteenth to three thirty-seconds in diameter, and colored greyed-brown (greyed-brown 99A)

Stem: Emerging young stems maroon (red-purple 178A) turning light gray (grayed-green 197B); glabrous; branches of an eight year old tree are three to eleven feet in length and three-quarters inch to three inches in diameter, measured at a distance of six inches from the main trunk; branches arise randomly at a typical branch angle of sixty to ninety degrees from the main trunk, branches on this tree were spaced four to fifteen inches apart.

Trunk: Smooth light grey (greyed-green 197B) becoming slightly fissured and darker on older sections.

Growth habit: Upright, oval.

Vigor: The initially discovered tree and young rooted plants have been observed to grow about three feet in height each year, and the trunk diameter has been observed to increase in caliper one inch each year after the first year.

Propagation: Holds to distinguishing characteristics through succeeding propagation by rooted cuttings.

Disease and pest resistance: Young propagative material sometimes observed with powdery mildew on the upper leaf surface during exceedingly wet weather; gall insects sometimes found on small branches; no other diseases or insects observed on trees to date.

I claim:

1. A new and distinct variety of Live Oak tree named 'SDLN', substantially as herein shown and described.

* * * * *

UNITED STATES PATENT AND TRADEMARK OFFICE

CERTIFICATE OF CORRECTION

PATENT NO. : PP 12,015 E
DATED : July 24, 2001
INVENTOR(S) : Anthony Brent Reeves It is certified that error appears in the above-identified patent and that said Letters Patent is hereby corrected as shown below:

Column 4,
Line 12, the word "surfave" should be -- surface --

Signed and Sealed this

Seventh Day of May, 2002

*Attest:*

*Attesting Officer*

JAMES E. ROGAN
*Director of the United States Patent and Trademark Office*

UNITED STATES PATENT AND TRADEMARK OFFICE

CERTIFICATE OF CORRECTION

PATENT NO. : PP 12,015 P2
DATED : July 24, 2001
INVENTOR(S) : Anthony Brent Reeves It is certified that error appears in the above-identified patent and that said Letters Patent is hereby corrected as shown below:

Column 4,
Line 12, the word "surfave" should be -- surface --

This certificate supersedes Certificate of Correction issued May 7, 2002

Signed and Sealed this

Seventh Day of May, 2002

*Attest:*

*Attesting Officer*

JAMES E. ROGAN
*Director of the United States Patent and Trademark Office*